(12) United States Patent
Wei et al.

(10) Patent No.: US 11,358,143 B2
(45) Date of Patent: Jun. 14, 2022

(54) COMPOSITIONS, DEVICES, AND METHODS OF MITIGATING LIPOPROTEIN INTERFERENCE IN IN VITRO DIAGNOSTIC ASSAYS FOR HYDROPHOBIC ANALYTES

(71) Applicant: Siemens Healthcare Diagnostics Inc., Tarrytown, NY (US)

(72) Inventors: Tie Wei, Wilmington, DE (US); Jie Li, Middletown, DE (US); Yun Yue, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/310,469

(22) PCT Filed: Jan. 15, 2020

(86) PCT No.: PCT/US2020/013629
§ 371 (c)(1),
(2) Date: Aug. 5, 2021

(87) PCT Pub. No.: WO2020/190358
PCT Pub. Date: Sep. 24, 2020

(65) Prior Publication Data
US 2022/0040693 A1      Feb. 10, 2022

Related U.S. Application Data

(60) Provisional application No. 62/820,409, filed on Mar. 19, 2019.

(51) Int. Cl.
*B01L 3/00*        (2006.01)
*G01N 33/92*       (2006.01)

(52) U.S. Cl.
CPC ........ *B01L 3/502715* (2013.01); *G01N 33/92* (2013.01); *B01L 2200/16* (2013.01); *B01L 2300/087* (2013.01); *G01N 2333/92* (2013.01)

(58) Field of Classification Search
CPC .. B01L 3/502715; B01L 3/5027; B01L 3/502; B01L 3/50; B01L 2200/16; B01L 2200/00; B01L 2300/087; B01L 2300/0861; B01L 2300/08
USPC .......................................... 422/502, 500, 50
See application file for complete search history.

(56) References Cited

U.S. PATENT DOCUMENTS

| | | |
|---|---|---|
| 2009/0188812 A1 | 7/2009 | Broughall et al. |
| 2010/0274155 A1 | 10/2010 | Battreil et al. |
| 2011/0086373 A1 | 4/2011 | Wallace-Davis et al. |
| 2017/0014822 A1* | 1/2017 | Ker .................. G01N 27/3272 |
| 2017/0356922 A1 | 12/2017 | Bahar et al. |
| 2018/0024124 A1 | 1/2018 | Wu et al. |

FOREIGN PATENT DOCUMENTS

| | | |
|---|---|---|
| CN | 101027559 | 8/2007 |
| CN | 107002017 | 8/2017 |
| CN | 108627510 | 10/2018 |
| JP | 2009520974 | 5/2009 |
| JP | 2010535346 | 11/2010 |
| JP | 2018501485 | 1/2018 |

OTHER PUBLICATIONS

International Search Report for PCT/US2020/013629 dated Apr. 9, 2020.
G. MacFarlane et al. "A simplified whole blood enzyme-linked immunosorbent assay (ProTrac II) for tacrolimus (FK506) using proteolytic extraction in place of organic solvents", Ther Drug Monit, 1996, vol. 18, Nr. 6, pp. 698-705 (Abstract only).

* cited by examiner

*Primary Examiner* — Christine T Mui

(57) ABSTRACT

Methods of mitigating lipoprotein interference in in vitro diagnostic assays for target hydrophobic analytes are disclosed, as well as compositions, kits, and devices useful in said methods. A pretreatment reagent is utilized that includes at least one enzyme that digests lipoprotein.

16 Claims, No Drawings

COMPOSITIONS, DEVICES, AND METHODS OF MITIGATING LIPOPROTEIN INTERFERENCE IN IN VITRO DIAGNOSTIC ASSAYS FOR HYDROPHOBIC ANALYTES

CROSS REFERENCE TO RELATED APPLICATIONS/INCORPORATION BY REFERENCE STATEMENT

Not Applicable.

STATEMENT REGARDING FEDERALLY SPONSORED RESEARCH OR DEVELOPMENT

Not Applicable.

BACKGROUND

In vitro diagnostic assays are used for the detection of hydrophobic analytes in biological samples. However, lipoproteins (such as, but not limited to, low density lipoprotein (LDL), very low density lipoprotein (VLDL), intermediate density lipoprotein (IDL), high density lipoprotein (HDL), and chylomicrons, etc. that are often quantitated by their cholesterol content) present in biological samples are known to interfere with such assays, especially for small hydrophobic analytes (such as, but not limited to, hydrophobic drugs and hormones). Currently there are no methods to eliminate this interference, because these hydrophobic haptens, when present in hydrophilic blood or serum, tend to insert themselves into the hydrophobic core of lipoprotein particles. As such, a negative interference by lipoproteins (cholesterol) is often observed because some of the analyte is tied up in the lipoprotein particles and thus unavailable to the assay reagents.

Current attempts at overcoming cholesterol or lipoprotein interference involve extraction of the analyte using organic solvent. This approach breaks down the lipoprotein so that the hydrophobic analyte becomes dissolved in the organic solvent. However, the extraction steps must be performed manually, and thus are not amenable for mitigating interference in assays performed on fully automated analyzers.

In another approach, organic solvent or detergent is added to the reagent mixture to help solubilize the analyte and partially prevent it from entering into the hydrophobic core of lipoprotein particles. However, mitigation of lipoprotein interference by this approach is limited and cannot completely remove lipoprotein interference.

An ELISA assay was previously developed for the small, immunosuppressive drug tacrolimus (also known as FK506) that utilizes proteinase to digest the immunophilin FK506-binding protein (FKBP) and thus free up any tacrolimus bound by FKBP. However, the use of proteinase to digest protein has limited effect on cholesterol/lipoprotein interference in the assay.

Thus, new and improved methods of mitigating lipoprotein interference, especially for use with automated analyzers are needed. It is to such methods, as well as compositions, kits, and devices utilized in same, that the present disclosure is directed.

DETAILED DESCRIPTION

Before explaining at least one embodiment of the inventive concepts in detail by way of exemplary language and results, it is to be understood that the inventive concepts are not limited in their application to the details of construction and the arrangement of the components set forth in the following description. The inventive concepts are capable of other embodiments or of being practiced or carried out in various ways. As such, the language used herein is intended to be given the broadest possible scope and meaning, and the embodiments are meant to be exemplary—not exhaustive. Also, it is to be understood that the phraseology and terminology employed herein is for the purpose of description only and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the inventive concepts as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety, and coating one moiety on another moiety, for example.

The term "sample" as used herein will be understood to include any type of biological sample that may be utilized in accordance with the present disclosure. Examples of fluidic biological samples that may be utilized include, but are not limited to, whole blood or any portion thereof (including, but not limited to, plasma or serum), whole or lysed blood cells (including, but not limited to, whole or lysed red blood cells), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "hapten" as used herein refers to a small proteinaceous or non-protein antigenic determinant (or "epitope") which is capable of being recognized in an in vitro diagnostic assay (which may involve a target analyte-specific binding partner, such as (but not limited to) an antibody).

The term "analyte" refers to a molecule that is capable of being recognized in an in vitro diagnostic assay (which may involve a target analyte-specific binding partner, such as (but not limited to) an antibody). When the assay is an immunoassay, the analyte comprises at least one antigenic determinant or "epitope," which is the region of the analyte which binds to the target analyte-specific binding partner (i.e., antibody). When the analyte is a hapten, the entire hapten molecule typically forms the epitope.

The term "target analyte-specific binding partner" as used herein will be understood to refer to any molecule capable of specifically associating with the target analyte. For example but not by way of limitation, the binding partner may be an antibody, a receptor, a ligand, aptamers, molecular imprinted polymers (i.e., inorganic matrices), combinations or derivatives thereof, as well as any other molecules capable of specific binding to the target analyte.

The term "antibody" is used herein in the broadest sense and refers to, for example, intact monoclonal antibodies and polyclonal antibodies, multi-specific antibodies (e.g., bispecific antibodies), antibody fragments and conjugates thereof that exhibit the desired biological activity of analyte binding (such as, but not limited to, Fab, Fab', F(ab')2, Fv, scFv, Fd, diabodies, single-chain antibodies, and other antibody fragments and conjugates thereof that retain at least a portion of the variable region of an intact antibody), antibody substitute proteins or peptides (i.e., engineered binding proteins/peptides), and combinations or derivatives thereof. The antibody can be of any type or class (e.g., IgG, IgE, IgM, IgD, and IgA) or sub-class (e.g., IgG1, IgG2, IgG3, IgG4, IgA1, and IgA2).

The term "microfluidics device" as used herein includes any device(s) capable of performing at least one diagnostic assay as described herein. The microfluidics device will typically be inserted into a system that automates the performance of the diagnostic assay(s). In one non-limiting embodiment, the microfluidics device is constructed for use in automated diagnostic assays conducted by, for example but not by way of limitation, one of the DIMENSION® integrated chemistry systems commercially available from Siemens Healthcare Diagnostics, Inc. (Newark, Del.). However, it will be understood that the microfluidics device can be any commercially available product described or otherwise contemplated herein that is capable of performing one or more diagnostic assays in accordance with the present disclosure. In addition, the microfluidics device may include multiple compartments that integrate multiple assays onboard a single microfluidics device used with a clinical chemistry system, so that a single amount of a biological sample is inserted into the microfluidics device and then delivered to multiple assay compartments.

Turning now to the inventive concepts, certain non-limiting embodiments of the present disclosure relate generally to compositions, kits, devices, and methods for improving the performance and reliability of in vitro diagnostic assays for hydrophobic analytes. In particular, certain embodiments of the present disclosure are related to compositions, kits, devices, and methods for mitigating lipoprotein interference in in vitro diagnostic assays for hydrophobic analytes.

Certain non-limiting embodiments of the present disclosure are directed to methods for detecting the presence and/or concentration of a target hydrophobic analyte in a biological sample. In certain particular (but non-limiting) embodiments, the methods may be further defined as methods of minimizing lipoprotein interference in in vitro diagnostic assays for hydrophobic analytes.

The methods include combining, either simultaneously or wholly or partially sequentially: (1) a sample suspected of containing the target hydrophobic analyte; (2) a pretreatment reagent comprising at least one enzyme that digests lipoprotein (such as, but not limited to, lipase and/or at least one other digestive enzyme (such as, but not limited to, stomach enzymes such as (but not limited to) pepsin and pancreatic enzymes such as (but not limited to) amylase and protease); and (3) at least one assay reagent capable of detecting a hydrophobic analyte. The method further includes performing one or more detection assays based on (3) and determining a concentration of target hydrophobic analyte present in the sample.

When (1) and (2) are incubated together, the enzyme present in the pretreatment reagent digests lipid and protein in the lipoprotein. This causes release of target analyte from the hydrophobic core of a lipoprotein particle so that the target analyte becomes accessible to the assay reagent(s) (i.e., such as, but not limited to, antibodies that specifically recognize the target analyte). As such, the target analyte is detected at an increased efficiency compared to assays in which the pretreatment reagent is not utilized, thereby providing a more robust assay for the target analyte.

One or more of the method steps can be performed manually; alternatively, the method steps may be fully automated on a clinical chemistry analyzer system, as described herein.

Any biological sample known in the art for use with in vitro diagnostic assays as described herein may be utilized in accordance with the present disclosure. Examples of biological samples that may be utilized include, but are not limited to, urine, whole blood or any portion thereof (including, but not limited to, plasma or serum), whole (i.e., substantially unlysed) or lysed blood cells (including, but not limited to, whole or lysed red blood cells), saliva, sputum, cerebrospinal fluid (CSF), intestinal fluid, intraperitoneal fluid, cystic fluid, sweat, interstitial fluid, tears, mucus, bladder wash, semen, combinations, and the like. Any hydrophobic analytes capable of detection via the assay methods disclosed or otherwise contemplated herein may be detected via the methods of the present disclosure. Examples of target analytes include small hydrophobic molecules such as (but not limited to) vitamin D, tacrolimus, sirolimus, everolimus, estrogen, estrone, estradiol, estriol, alfatradiol (estradiol, estrone, and estriol), cyclosporine, ethinylestradiol, esterified estrogens, moxestrol, qunestrol, progestins, progesterone, androgens such as testosterone, dihydroteestosterione (DHT), dehydroepiandrosterone (DHEA) and DHEA sulfate (DEHE-S), androstenendione aldosterone, other steroid hormones, cortisol, catecholamine, 25-hydroxy Vitamin D2 (25-OH Vitamin D2), 25-hydroxy Vitamin D3 (25-OH Vitamin D3), 1,25-dihydroxy Vitamin D2 (1,25-OH Vitamin D2), and 1,25-dihydroxy Vitamin D3 (1,25-OH Vitamin D3), and the like.

The pretreatment reagent comprises at least one enzyme that digests lipids on lipoprotein into more water soluble and smaller compounds; said enzyme may be lipase and/or at least one other digestive enzyme (such as, but not limited to, stomach enzymes such as (but not limited to) pepsin and pancreatic enzymes such as (but not limited to) amylase and protease). In addition, the pretreatment reagent may comprise one or more additional substances that function to enhance enzymatic activity. Non-limiting examples of additional substances that may be present in the pretreatment reagent include at least one cofactor for the enzyme (such as, but not limited to, bile acid and/or a salt thereof), at least one surfactant (such as, but not limited to, PLURONIC® block copolymer (BASF Corporation, Ludwigshafen, Germany), or at least one protease, as well as any combination thereof.

The enzyme that digests lipoprotein must be provided at a sufficient concentration so as to cause the hydrophobic core of a lipoprotein particle to release the target analyte so that it becomes accessible to the assay reagent(s), thereby allowing for detection of the target analyte at increased efficiency. The concentration of enzyme will be dependent upon the amount of analyte present and the time of the pretreatment reaction.

The enzyme(s) that digests lipoprotein is present in the pretreatment reagent may be present at any concentration that allows the enzyme to function as described herein. Examples of particular concentrations include, but are not limited to: about 0.01 mg/mL, about 0.05 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, or higher. In a particular (but non-limiting) embodiment, the concentration of the enzyme in the pretreatment reagent is defined as being within a range of any two of the values shown herein above, such as (but not limited to) a range of from about 0.01 mg/mL to about 100 mg/mL, a range of from about 0.05 mg/mL to about 50 mg/mL, a range of from about 0.1 mg/mL to about 20 mg/mL, a range of from about 0.5 mg/mL to about 10 mg/mL, and the like. However, it is to be understood that the specific concentration ranges listed above are for illustration purposes only and are not to be considered limiting; any concentration range having a lower limit of one of the values listed above and an upper limit of another of the values listed above explicitly falls within the scope of the present disclosure.

Similarly, each of the one or more additional substances of the pretreatment reagent may be present at any concentration that allows the substance(s) to function to enhance enzymatic activity. For example, each of the additional substances (such as, but not limited to, the enzyme cofactor like bile acid and/or a salt thereof, the surfactant like PLURONIC® block copolymer, or a protease), may be provided at a concentration selected from the following non-limiting examples of concentrations: about 0.001%, about 0.005%, about 0.01%, about 0.02%, about 0.03%, about 0.04%, about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.25%, about 3.5%, about 3.75%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, and higher. In a particular (but non-limiting) embodiment, the concentration of each additional substance present in the pretreatment reagent is defined as being within a range of any two of the values shown herein above, such as (but not limited to) a range of from about 0.001% to about 25%, a range of from about 0.005% to about 15%, a range of from about 0.01% to about 5%, and the like. However, it is to be understood that the specific concentration ranges listed above are for illustration purposes only and are not to be considered limiting; any concentration range having a lower limit of one of the values listed above and an upper limit of another of the values listed above explicitly falls within the scope of the present disclosure.

In certain non-limiting embodiments, the at least one assay reagent capable of detecting a hydrophobic analyte is an immunoassay reagent (i.e., a target analyte-specific binding partner (such as, but not limited to, an antibody). The at least one target analyte-specific binding partner is then allowed to bind to the target analyte or the at least one immunoassay reagent.

The pretreatment and assay/detection steps may be performed in the same compartment of a microfluidics device. Alternatively, the pretreatment step may be performed in a first compartment, and then the pretreated sample transferred to a second compartment for performing the detection step.

The biological sample may be added to the pretreatment step in its native form, or the biological sample may be lysed prior to the pretreatment step. Thus, in a particular (but non-limiting) embodiment, the methods described or otherwise contemplated herein may further include the steps of lysing a biological sample in a first compartment and then transferring the lysed biological sample to a second compartment utilized in the pretreatment step.

Any of the method steps described herein may be performed, for example but not by way of limitation, by a user. However, as used herein, the term "user" is not limited to use by a human being; rather, the term "user" may comprise (for example, but not by way of limitation) a computer, a server, a website, a processor, a network interface, a human, a user terminal, a virtual computer, combinations thereof, and the like.

Certain non-limiting embodiments of the present disclosure are directed to reagent kits useful for conveniently performing the diagnostic assay methods described herein above. The reagent kit includes one or more of any of the pretreatment reagents described or otherwise contemplated herein in combination with one or more of any of the assay reagents capable of detecting a hydrophobic analyte as described or otherwise contemplated herein.

Certain other non-limiting embodiments of the present disclosure are directed to an assay device (such as, but not limited to, a microfluidics device) which contains at least one of any of the pretreatment reagents described or otherwise contemplated herein and at least one of any of the assay reagents described or otherwise contemplated herein, and wherein the assay device is for use in any of the in vitro diagnostic assay methods described herein above.

For example, a microfluidics device may include at least one compartment capable of receiving a sample suspected of containing a target hydrophobic analyte, wherein the at least one compartment includes at least one of the pretreatment reagents as described in detail herein above. The compartment may further contain one or more of any of the assay reagents described or otherwise contemplated herein. Alternatively, the microfluidics device may be provided with at least a second compartment that is capable of being in fluidic communication with the first compartment containing the pretreatment reagent, and the assay reagent(s) may be included in the second compartment. The second compartment may be a read chamber where the detection assay for determining a concentration of target hydrophobic analyte present in the sample is performed; alternatively, the microfluidics device may additionally include a read chamber capable of being in fluidic communication with the second compartment.

In addition, the reagent kits and/or microfluidics devices of the present disclosure may further contain other component(s) and/or reagent(s) for conducting any of the particular diagnostic assays described or otherwise contemplated herein. The nature of these additional component(s)/reagent(s) will depend upon the particular assay format, and identification thereof is well within the skill of one of ordinary skill in the art. Examples of additional reagents/components that may be present in the reagent kits and/or microfluidics devices of the present disclosure include, but are not limited to, diluents, lysing agents (for lysing red blood cells), wash solutions (such as but not limited to, isotonic solutions), positive controls, negative controls, quality controls, and/or actuators, as well as any combination thereof.

The relative amounts of the various components/reagents in the kits and/or microfluidics devices can vary widely to provide for concentrations of the components/reagents that substantially optimize the reactions that need to occur during the assay methods and further to optimize substantially the sensitivity of an assay.

The reagent kits of the present disclosure may further include a set of written instructions explaining how to use the kit. A kit of this nature can be used with any of the microfluidics devices and/or in any of the methods described or otherwise contemplated herein.

The microfluidics device may have one or more manual functions associated therewith (i.e., wherein pipetting is required for addition of one or more reagents and/or movement of a mixture between two compartments); alternatively, the microfluidics device may be a fully automatic, closed system in which the necessary reagents/components are disposed in various compartments during construction of the device (wherein the various compartments are in continuous fluidic communication (or are capable of being in continuous fluidic communication)), and thus no manual manipulation of the sample and/or reagent(s) is required for performance of the assay after the sample is added to the microfluidics device.

As described herein above, the microfluidics device comprises one or more compartments containing the components/reagents described herein above. However, it will be understood that the microfluidics device may be provided with any number of compartments, any arrangement of compartments, and any distribution of the components/reagents therebetween, so long as the device is able to function in accordance with the present disclosure. When provided with multiple compartments, the compartments may be completely separated from one another, or one or more compartments may be capable of being in fluidic communication with one another. Various structures of microfluidics devices that are capable of use in accordance with the present disclosure are well known in the art, and therefore no further description thereof is deemed necessary.

In certain embodiments, the microfluidics device includes at least first and second compartments. The first compartment is capable of receiving a biological sample and, if desired (but not by way of limitation), may include a mechanism for lysing red blood cells or otherwise preparing the sample for pretreatment and assay. Said separation mechanisms are well known in the art of microfluidics devices, and therefore no further description thereof is deemed necessary. The second compartment is capable of being in fluidic communication with the first compartment and includes the at least one pretreatment reagent. The second compartment may further include the at least one assay reagent; alternatively, the microfluidics device may include a third compartment for storage of the at least one assay reagent, and wherein the at least one assay reagent can be transferred from the third compartment into the second compartment following incubation of the sample with the pretreatment reagent in a pretreatment step.

The microfluidics device may also include a read chamber (such as, but not limited to, an optical read chamber) that is capable of being interrogated by a clinical chemistry system (such as, but not limited to, optically interrogated by a spectrometer). The read chamber may be associated with any of the compartments described herein above, or the read chamber may be associated with a separate compartment from those described herein above.

The inlet channel and a compartment, as well as two compartments, may be described as being "capable of being in fluidic communication" with one another; this phrase indicates that the compartment(s) may still be sealed, but the two compartments are capable of having fluid flow therebetween upon puncture of a seal formed therein or therebetween.

The kits/microfluidics devices of the present disclosure may be provided with any other desired features known in the art or otherwise contemplated herein. For example, but not by way of limitation, the kits/microfluidics devices of the present disclosure may further include one or more additional compartments containing other solutions, such as but not limited to, lysing agents (for lysing red blood cells), diluents, wash solutions, labeling agents, interference solutions, positive controls, negative controls, quality controls, and/or actuators, as well as any combination thereof.

Example

An Example is provided hereinbelow. However, the present disclosure is to be understood to not be limited in its application to the specific experimentation, results, and laboratory procedures disclosed herein. Rather, this Example is simply provided as one of various embodiments and is meant to be exemplary, not exhaustive.

In this Example, the effects of the use of pretreatment reagents on cholesterol interference in an everolimus (EVRO) assay on a DIMENSION® integrated chemistry system (Siemens Healthcare Diagnostics, Inc., Newark, Del.) were examined. Varying amounts of lipase, bile salt (as a cofactor for lipase), and PLURONIC® block copolymer (BASF Corporation, Ludwigshafen, Germany) were spiked in pretreatment reagents that were incubated with samples containing known amounts of cholesterol prior to performing an everolimus (EVRO) assay of the treated sample on a DIMENSION® integrated chemistry system (Siemens Healthcare Diagnostics, Inc., Newark, Del.).

As shown in Table 1, in the absence of a pretreatment step, the amount of cholesterol interference observed in the EVRO assay was −7.6%, −12%, and −19% for cholesterol concentrations of 300 mg/mL, 350 mg/mL, and 400 mg/mL, respectively. The addition of a pretreatment step with a reagent comprising lipase, its cofactor bile acid/salt (for enzymatic activity enhancement), and PLURONIC® as surfactant decreased the amount of cholesterol interference to 1% (from −7.6%), −0.4% (from −12%), and −3% (from −19%) at cholesterol concentrations of 300 mg/mL, 350 mg/mL, and 400 mg/mL, respectively. As such, cholesterol interference was substantially eliminated at 400 mg/mL cholesterol using the compositions and methods of the present disclosure.

TABLE 1

Effect of Lipase on Cholesterol Interference Mitigation

| Lipase mg/mL | 0 | 5 | 5 | 3 | 5 |
|---|---|---|---|---|---|
| % Bile salt | 0% | 0.1% | 0.1% | 0.1% | 0.05% |
| % Pluronic | 0.9% | 0.9% | 0% | 0% | 0% |

TABLE 1-continued

Effect of Lipase on Cholesterol Interference Mitigation

| Lipase mg/mL | 0 | 5 | 5 | 3 | 5 |
|---|---|---|---|---|---|
| 300 mg/mL Cholesterol | −7.6% | 1.0% | −0.6% | 0.5% | −1.6% |
| 350 mg/mL Cholesterol | −12.0% | −0.4% | 0.6% | −6.9% | −4.3% |
| 400 mg/mL Cholesterol | −19.0% | −3.0% | −5.4% | −5.6% | −6.9% |

Thus, in accordance with the present disclosure, there have been provided compositions, kits, and devices, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed inventive concepts.

What is claimed is:

1. A microfluidics device for use in a clinical chemistry instrument, the microfluidics device comprising:
   at least one compartment capable of receiving a sample suspected of containing a target hydrophobic analyte, wherein the at least one compartment comprises:
      a pretreatment reagent that digests lipoprotein particles, wherein the pretreatment reagent comprises protease, lipase, and a cofactor for lipase; and
      at least one assay reagent capable of detecting a hydrophobic analyte for determining a concentration of target hydrophobic analyte present in the sample.

2. The microfluidics device of claim 1, wherein the microfluidics device is further defined as comprising at least two compartments, wherein the pretreatment reagent is disposed in a first compartment that is capable of receiving the sample, and the at least one assay reagent is disposed in a second compartment that is capable of being in fluidic communication with the first compartment, and wherein the second compartment is a read chamber in which the detection assay for determining a concentration of target hydrophobic analyte present in the sample is performed.

3. The microfluidics device of claim 1, wherein lipase is present in the pretreatment reagent at a concentration in a range of from about 0.1 mg/mL to about 20 mg/mL.

4. The microfluidics device of claim 1, wherein the target hydrophobic analyte is selected from the group consisting of vitamin D, tacrolimus, sirolimus, everolimus, estrogen, estrone, estradiol, estriol, alfatradiol, cyclosporine, ethinylestradiol, esterified estrogens, moxestrol, quinestrol, progestins, progesterone, androgens, testosterone, dihydrotestosterone (DHT), dehydroepiandrosterone (DHEA), DHEA sulfate, androstenedione, aldosterone, cortisol, catecholamine, 25-hydroxy Vitamin D2, 25-hydroxy Vitamin D3, 1,25-dihydroxy Vitamin D2, and 1,25-dihydroxy Vitamin D3.

5. The microfluidics device of claim 1, wherein the at least one assay reagent is further defined as an immunoassay reagent.

6. The microfluidics device of claim 1, wherein the cofactor for lipase comprises bile acid and/or a salt thereof.

7. The microfluidics device of claim 1, wherein the pretreatment reagent further comprises a surfactant.

8. The microfluidics device of claim 1, wherein the pretreatment reagent further comprises pepsin.

9. The microfluidics device of claim 1, wherein the pretreatment reagent further comprises amylase.

10. A microfluidics device for use in a clinical chemistry instrument, the microfluidics device comprising:
    at least one compartment capable of receiving a sample suspected of containing a target hydrophobic analyte, wherein the at least one compartment comprises:
       a pretreatment reagent that digests lipoprotein particles, wherein the pretreatment reagent comprises protease, lipase, and bile acid and/or a salt thereof; and
       at least one assay reagent capable of detecting a hydrophobic analyte for determining a concentration of target hydrophobic analyte present in the sample.

11. The microfluidics device of claim 10, wherein the pretreatment reagent further comprises at least one additional substance, wherein the at least one additional substance is selected from the group consisting of amylase, pepsin, a surfactant, and combinations thereof.

12. The microfluidics device of claim 10, wherein lipase is present in the pretreatment reagent at a concentration in a range of from about 0.1 mg/mL to about 20 mg/mL.

13. The microfluidics device of claim 10, wherein the target hydrophobic analyte is selected from the group consisting of vitamin D, tacrolimus, sirolimus, everolimus, estrogen, estrone, estradiol, estriol, alfatradiol, cyclosporine, ethinylestradiol, esterified estrogens, moxestrol, quinestrol, progestins, progesterone, androgens, testosterone, dihydrotestosterone (DHT), dehydroepiandrosterone (DHEA), DHEA sulfate, androstenedione, aldosterone, cortisol, catecholamine, 25-hydroxy Vitamin D2, 25-hydroxy Vitamin D3, 1,25-dihydroxy Vitamin D2, and 1,25-dihydroxy Vitamin D3.

14. The microfluidics device of claim 10, wherein the at least one assay reagent is further defined as an immunoassay reagent.

15. A microfluidics device for use in a clinical chemistry instrument, the microfluidics device comprising:
    at least one compartment capable of receiving a sample suspected of containing a target hydrophobic analyte, wherein the at least one compartment comprises:
       a pretreatment reagent that digests lipoprotein particles, wherein the pretreatment reagent comprises protease, lipase, bile acid and/or a salt thereof, and at least one surfactant; and
       at least one immunoassay reagent capable of detecting a hydrophobic analyte for determining a concentration of target hydrophobic analyte present in the sample.

16. The microfluidics device of claim 15, wherein the target hydrophobic analyte is selected from the group consisting of vitamin D, tacrolimus, sirolimus, everolimus, estrogen, estrone, estradiol, estriol, alfatradiol, cyclosporine, ethinylestradiol, esterified estrogens, moxestrol, quinestrol, progestins, progesterone, androgens, testosterone, dihydrotestosterone (DHT), dehydroepiandrosterone (DHEA), DHEA sulfate, androstenedione, aldosterone, cortisol, catecholamine, 25-hydroxy Vitamin D2, 25-hydroxy Vitamin D3, 1,25-dihydroxy Vitamin D2, and 1,25-dihydroxy Vitamin D3.

* * * * *